United States Patent [19]

Renga

[11] Patent Number: 4,642,349

[45] Date of Patent: Feb. 10, 1987

[54] PROCESS FOR MAKING AROMATIC ETHERS

[75] Inventor: James M. Renga, Midland, Mich.

[73] Assignee: The Dow Chemical Company, Midland, Mich.

[21] Appl. No.: 381,239

[22] Filed: May 24, 1982

Related U.S. Application Data

[63] Continuation-in-part of Ser. No. 187,688, Sep. 16, 1980, abandoned.

[51] Int. Cl.$^4$ .................... C07D 213/61; C07C 41/16; C07C 41/01

[52] U.S. Cl. ...................................... 546/302; 560/61; 568/586; 568/585; 568/630; 568/631; 568/656; 568/657

[58] Field of Search ................ 546/302; 568/630, 631, 568/656, 657, 585, 586; 560/61

[56] References Cited

U.S. PATENT DOCUMENTS 4,254,276  3/1981  Iori et al. ............................... 560/64

Primary Examiner—Alan L. Rotman

[57] ABSTRACT

Aromatic ethers or polyethers are prepared by reacting an organic halide such as a hydrocarbon halide with an aryl lower alkyl carbonate in the presence of an initiator.

10 Claims, No Drawings

PROCESS FOR MAKING AROMATIC ETHERS

CROSS-REFERENCE TO RELATED APPLICATION

This is a continuation-in-part of copending application Ser. No. 187,688, filed Sept. 16, 1980, now abandoned.

BACKGROUND OF THE INVENTION

This invention concerns a new chemical process for making aromatic ethers. Ethers thereby obtained have various uses, for example, as chemical intermediates, as heat transfer media, and as herbicides. Polymeric ethers preparable by this process are useful moldable plastics.

A common conventional method for making aromatic ethers involves the reaction of a metal salt of an aromatic hydroxy compound with an alkyl or aryl halide. Alkyl sulfates and sulfonates can also be used as alkylating agents in this kind of reaction. In some cases, a phenol can be reacted with an alcohol in the presence of a strong acid to produce the alkyl phenyl ether. In all of these conventional methods, the reaction mixture is either basic or acidic and contains an inorganic impurity, i.e., a metal salt or a spent acid which must be separated from the ether product and discarded.

It is known that phenyl alkyl carbonates can be thermally decomposed to form mixtures of products including the phenol and the phenyl alkyl ether. However, the decomposition is slow and usually incomplete and requires high temperatures or long heating times. The decomposition of cyclic carbonates such as ethylene carbonate and propylene carbonate to form ethylene oxide and propylene oxide respectively is known to be catalyzed by sulfonium and phosphonium salts and some metal salts (see Wu, U.S. Pat. No. 4,069,234).

SUMMARY OF THE INVENTION

It has now been found that an aryl lower alkyl or aryl halogenated lower alkyl carbonate of the formula $Ar(OCO_2R)_m$ reacts with a reactive aryl, alkyl, or heterocyclic organic halide of the formula $R'X_n$ in the presence of an initiator at about 50° C.–250° C. to produce a high yield of the corresponding aryl organic ether with elimination of the relatively volatile lower alkyl halide and $CO_2$ as coproducts of the reaction.

In the above formulas, m and n are each an integer from one to about three and represent the valences of the groups Ar and R'. Ar is any carbocyclic or heterocyclic aromatic group, unsubstituted or substituted with one or more groups unreactive in the reaction, R is a lower alkyl or halogenated lower alkyl group, R' is an aliphatic, cycloaliphatic, aromatic, or heterocyclic group, saturated or unsaturated, unsubstituted or substituted with one or more groups unreactive in the reaction, and X is Cl, Br, or I.

DETAILED DESCRIPTION OF THE INVENTION

Depending upon the values of m and n in the above formulas, the reaction produces a monoether or polyether as shown in the following equation:

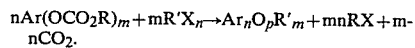

$Ar_nO_pR'_m$ is an empirical formula representing different kinds of ethers. In the formula p is an integer equal to the product of m and n. When, as preferred, both m and n are one or one of m and n is one and the other is two, a monoether or a diether is the ether product. When both m and n are greater than one, preferably two, a polymeric polyether structure is produced.

In the above equation and formulas, a monovalent Ar can be phenyl, naphthyl, biphenylyl, pyridyl, furyl, quinolyl, benzofuryl, pyridazyl, indolyl, benzothiazolyl, or the like, unsubstituted or substituted with up to about three unreactive groups. Such substituents include lower alkyl, lower alkoxy, halo, nitro, ester groups, trifluoromethyl, aralkyl, and phenoxy. When m is greater than one, Ar represents the divalent or trivalent equivalents of the above, e.g., phenylene, naphthylylene, alkylidenediphenylene, alkylenetriphenylene, oxydiphenylene, and the like, also substituted or unsubstituted as described. Ar preferably represents groups where the aromatic portion is monocyclic such as phenyl, phenylene, alkylidenediphenylene, and pyridyl.

The groups represented by R' are also monovalent, divalent, and trivalent hydrocarbon and heterocyclic groups which may have unreactive substituents. Thus, R' can be an aliphatic, cycloaliphatic, aromatic, or heterocyclic group such as higher alkyl of about 6–20 carbon atoms; an olefinic group of about 3–20 carbon atoms such as allyl, butenyl, octenyl, hexadecenyl, pentadienyl, and octadienyl; an alicyclic group such as cyclopentyl and cyclohexyl; carbocyclic aryl and aralkyl groups such as phenyl, naphthyl, and benzyl; or a heterocyclic group such as pyridyl, furyl, quinolyl, indolyl, benzothiazolyl, benzofuryl, and the like; also the polyvalent equivalents of these, for example, hexylene, butenylene, cyclohexylene, and benzylidene, all of these unsubstituted or substituted with one or more inert substituents such as previously listed.

This process has particular value in that it offers a different reaction route for the preparation of commercially useful herbicidal ethers that avoids or minimizes the formation of undesirable by-products characteristically produced by conventional processes. Thus, when Ar is a polychlorophenyl or polychloropyridyl group and R' is a lower aliphatic carboxylic acid ester residue such as —$CH_2CO_2R$ or —$C_2H_4CO_2R$, the ether reaction product is the corresponding polychlorophenoxyalkanoate, for example, the esters commonly known as 2,4-D and 2,4,5-T, or similar polychloropyridoxyalkanoates.

In the reaction generally, R' is preferably of significantly higher molecular weight than R (which is usually a methyl group) so that the by-product RX is vaporized readily and leaves the reaction mixture substantially as the $CO_2$ comes off, thereby minimizing the undesirable side reaction of RX with the unreacted starting carbonate.

The reactive halogen X can be chlorine, bromine or iodine and is preferably chlorine. It is necessary that X be reactive in the process under the conditions described and such reactivity may be conferred by either the configuration of R' or by one or more activating substituents on R'. Thus, a normally unreactive chlorine atom on a benzene ring may be rendered reactive by one or more other substituents such as the nitro group.

The lower alkyl or halogenated lower alkyl group R in the above equation can be methyl, ethyl, propyl, butyl or halogenated derivatives thereof. By halogen is included fluoro, chloro, bromo and iodo. Most preferably R is a methyl group. The reaction proceeds with elimination of $CO_2$ and the volatile halide product RX.

Consequently, when RX is the highly volatile methyl chloride, the reaction is particularly accelerated and separation of the ether product is also thereby facilitated.

Although the process can be operated at any temperature in the broad range of about 50°–250° C. as previously stated, it is preferably carried out at about 100°–175° C. for most convenient operation conditions and reaction time. The reaction time can vary from about 0.1 hour to about 10 hours depending upon the reaction conditions.

A reaction solvent is usually not required or desirable, but use of a solvent may be advantageous under some conditions, e.g., when low boiling reactants or solid reaction products are involved. Polar solvents appear to increase the rate of reaction. Relatively high boiling inert solvents such as N,N-dimethylformamide, sulfolane, glycol diethers, and substituted aromatics such as anisole, o-dichlorobenzene, alkylated pyridines, and the like are preferred.

The reaction is initiated by the presence of one of several suitable initiators. Basic catalysts, such as alkali metal alkoxides, salts of a strong base and a weak acid, or non-nucleophilic organic bases are suitable. The latter class consists in practice of tertiary amines, both aliphatic and aromatic. Suitable basic catalysts include triethylamine, tributylamine, pyridine, quinoline, N,N-dimethylaminopyridine, alkali metal carbonates, acetates and alkoxides. Additional suitable initiators include alkali metal halides and stable quaternary salts such as ammonium or phosphonium quaternary salts having inert counterions. A preferred alkali metal halide is lithium chloride. Preferred quaternary salts have the general formula $(R'')_4AY$ where each $R''$ is a hydrocarbon moiety, A is a quaternary nitrogen or phosphorus atom, and Y is an inert (i.e., unreactive in this process) neutralizing anion which may be inorganic, e.g., chloride, bromide, iodide, bicarbonate, sulfate, or the like, or Y may be an organic ion such as formate, acetate, benzoate, phenate, or bisphenate. The $R''$ groups may be alkyl, aryl, alkaryl, aralkyl, or cycloalkyl. Also, two $R''$ groups may combine to form a heterocyclic ring. Illustrative quaternary salt catalysts are tetrabutylammonium iodide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and similar ammonium and phosphonium salts with these and other such inorganic and organic neutralizing anions as described above. The catalytic salt may be added as such to the reaction mixture or it may be formed in situ.

The quantity of initiator compound is not critical so long as any significant amount is present and available at the reaction site. Suitably from about 0.01–10 percent of initiator based on the weight of the reactants is used. Larger amounts of initiator may be employed but may complicate the ability to produce pure product.

The initiator should be at least partially soluble in the reaction mixture and it may be advantageous in accomplishing this goal to employ an additional agent to render the initiator soluble in the reaction medium. Suitable agents, referred to hereinafter as "solubilizing agents", which are particularly suitable for use with basic catalysts and alkali metal halides include the compounds generally known as phase-transfer catalysts such as, for example, hexamethylphosphoramide or the cyclic oligomers of ethylene oxide known as crown ethers. Such solubilizing agents may be employed in minor amounts, for example, in the ratio of about 0.005–10.0 mole per mole of initiator.

In a mode of the invention particularly adapted to continuous operation, one or more $R''$ groups of the quaternary salt may be pendant methylene groups from a resin matrix so that the quaternary salt is a salt form of a strong base anion-exchange resin such as DOWEX®21K, DOWEX®11, DOWEX®MWA-1, or other such commercially available ion-exchange resins or the phosphonium equivalents of such quaternary ammonium-substituted resins. In such a continuous operation of the process, the mixed reactants are passed at an appropriate flow rate through a bed of the strong base anion resin maintained at a suitable temperature within the limits previously defined.

Batchwise operation of the process involves simply combining the reactants and initiator and heating until the evolution of carbon dioxide and alkyl halide has ceased.

The process is ordinarily carried out at atmospheric pressure but it may be carried out at somewhat reduced pressure to hasten the removal by distillation of the volatile alkyl halide product. Passage of a stream of nitrogen or other inert gas through or over the reaction mixture may also be beneficial in this respect for some mixtures.

This process provides the advantages of a neutral reaction mixture, moderate temperature, and ready separation of the ether product as well as the alkyl halide coproduct. The volatile reaction products are carbon dioxide which can simply be vented and the alkyl halide which can be recovered by condensation or adsorption. The residue in the reaction vessel is primarily the desired ether together with the small amount of initiator and, in some cases, a minor amount of the alkyl phenyl ether produced by the decomposition of the alkyl phenyl carbonate reactant. The desired ether product is readily recovered and purified by conventional means such as distillation or recrystallization depending on its physical properties.

The aryl alkyl carbonate starting material can be made by any of several known methods for making these mixed esters. A common preparatory method is the reaction of a phenol or corresponding hydroxyl substituted heterocyclic compound such as a pyridinol with an alkyl chloroformate under basic conditions. Asymmetric carbonates can also be made by the acid or base catalyzed transesterification reaction of an alcohol or phenol with a symmetrical carbonate ester, for example, the reaction of phenol with dimethyl carbonate to make methyl phenyl carbonate and the corresponding reaction of a pyridinol to make the methyl pyridyl carbonate.

SPECIFIC EMBODIMENTS

The following examples are provided as further illustrative of the invention and are not to be construed as limiting.

EXAMPLE 1

A mixture of 3.8 g of methyl phenyl carbonate, 3.16 g of benzyl chloride, and 0.085 g of tetra-n-butyl phosphonium bromide (TBPB) was heated at 150° C. in a reaction flask for 3 hours. Carbon dioxide was evolved and analysis of the reaction mixture indicated a 99 percent conversion of the carbonate to a mixture of 96 percent benzyl phenyl ether and 4 percent anisole. Distillation produced a 95 percent yield of benzyl phenyl ether based on the starting reactants.

EXAMPLE 2

The procedure of Example 1 was repeated using 0.09 of tetra-n-butyl ammonium iodide as the initiator. After 6 hours at 150° C., 92 percent of the methyl phenyl carbonate had reacted to form a mixture of 96 percent benzyl phenyl ether and 4 percent anisole.

EXAMPLE 3

A mixture of 3.8 g of methyl phenyl carbonate, 3.06 g of ethyl chloroacetate, and 0.42 g of TBPB was heated at 120° C. for 2 hours. Distillation of the resulting reaction mixture provided a 96 percent yield of ethyl phenoxyacetate.

EXAMPLE 4

A mixture of 3.8 g of methyl phenyl carbonate, 3.63 g of allyl bromide, 0.17 g of TBPB, and 10 ml of sulfolane was stirred at 140° C. for 1.5 hours. Distillation of the resulting reaction mixture gave 2.9 g of a mixture of 91 percent allyl phenyl ether and 9 percent anisole.

EXAMPLE 5

A mixture of 3.2 g of methyl 2,4,5-trichlorophenyl carbonate, 1.53 g of ethyl chloroacetate, and 0.05 g of TBPB was heated at 120° C. After 20 minutes, 100 percent of the carbonate had been reacted with a 95 percent selectivity to ethyl 2,4,5-trichlorophenoxyacetate. Recrystallization of the product from an ether-hexane mixture gave 3.1 g (88 percent yield) of the purified ester.

EXAMPLES 6–14

Various mixtures of methyl phenyl carbonate, n-octyl bromide or chloride, and a tetra-n-butyl phosphonium salt were heated at 150° C. for 1–4 hours to produce an ether product according to the equation:

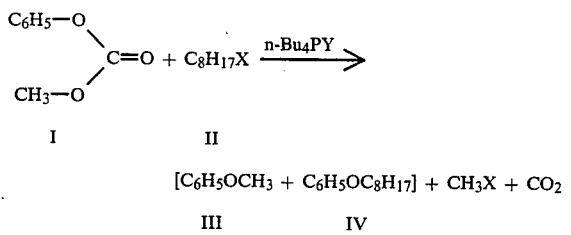

$$[C_6H_5OCH_3 + C_6H_5OC_8H_{17}] + CH_3X + CO_2$$

III           IV

Results are listed in Table I.

In Examples 6–14, with or without a solvent present, the product was predominantly octyl phenyl ether produced by the reaction of the octyl halide with methyl phenyl carbonate, the rest being anisole from the quaternary salt-initiated decomposition of methyl phenyl carbonate. Similar results were produced in the reactions of Examples 1–5 where either no solvent was used or the polar solvent sulfolane was the reaction medium (Example 4).

EXAMPLES 15–28

Methyl 3,5,6-trichloro-2-pyridyl carbonate was prepared by reacting methyl chloroformate with 3,5,6-trichloro-2-pyridinol at 0° C.–5° C. in the presence of an equivalent of pyridine as acid acceptor and using methylene chloride as the reaction solvent.

Mixtures of 2.56 g (0.01 g mole) of methyl 3,5,6-trichloro-2-pyridyl carbonate, 0.01 to 0.1 g mole of methyl chloroacetate, and initiator as noted were heated at 100° C. until gas evolution had stopped. Unreacted methyl chloroacetate was then removed from the reaction mixture using a rotary evaporator. The crude product remaining was analyzed by gas chromatography. In each case, a good yield (about 2.8 g of crude product) of the expected 3,5,6-trichloro-2-pyridoxyacetic acid, methyl ester (III) was found with only small amounts of by-products IV, V, and VI as shown schematically below.

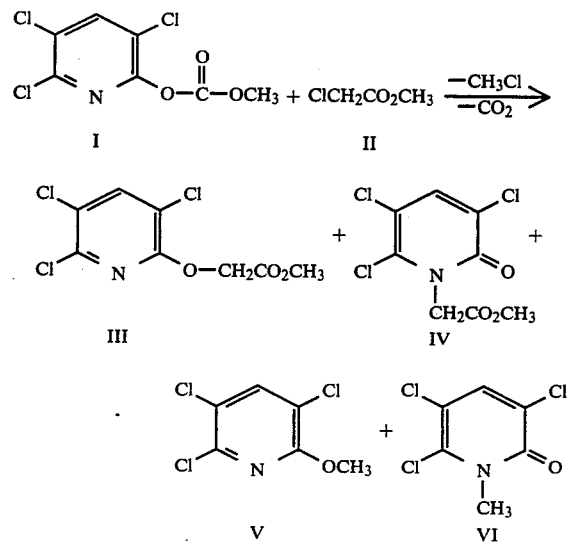

TABLE I

| Example No. | X | g moles I:II | Y | mole % Initiator* | Solvent, (ml) | Time Hrs. | % Conv. I | mole Ratio III:IV |
|---|---|---|---|---|---|---|---|---|
| 6 | Cl | .025:.025 | Br | 2.0 | none | 1 | 92 | 32:68 |
| 7 | Cl | " | Br | 0.4 | none | 4 | 41 | 30:70 |
| 8 | Br | " | Br | 2.0 | none | 1 | 87 | 32:68 |
| 9 | Br | " | Br | 0.4 | none | 4 | 52 | 28:72 |
| 10 | Cl | .0125:.0125 | Br | 2.0 | DMF** (15) | 1 | 93 | 37:63 |
| 11 | Cl | " | Br | 2.0 | n-decane (15) | 1 | 29 | 40:60 |
| 12 | Cl | " | formate | 2.0 | none | 1 | 92 | 24:76 |
| 13 | Cl | .0125:.03 | formate | 2.0 | none | 1 | 85 | 13:87 |
| 14 | Cl | " | acetate | 2.0 | none | 2 | 92 | 14:86 |

*based on the carbonate
**dimethylformamide

The reaction conditions and results are listed in detail in Table II.

TABLE II

| Example No. | Mole Ratio I:II | Initiator | Mole % Cat. | Time (hrs.) | Molar Ratio III:IV | Molar Ratio III:V + VI[1] |
|---|---|---|---|---|---|---|
| 15 | 1:1 | n-Bu$_4$PBr | 1 | 1.5 | 27:1 | 4.4:1 |
| 16 | 1:5 | n-Bu$_4$PBr | 1 | 1.0 | 33:1 | 26:1 |
| 17 | 1:10 | n-Bu$_4$PBr | 1 | 2.0 | 42:1 | 39:1 |
| 18 | 1:5 | n-Bu$_4$NCl | 1 | 0.5 | 35:1 | 22:1 |
| 19 | 1:5 | n-Bu$_4$NCl | 5 | <0.5 | 55:1 | 29:1 |
| 20 | 1:5 | BzPh$_3$PCl[2] | 1 | 1.0 | 43:1 | 25:1 |
| 21 | 1:5 | n-BuPh$_3$PHCO$_2$[2] | 1 | 0.25 | 37:1 | 22:1 |
| 22 | 1:5[3] | n-Bu$_4$PBr | 1 | 0.5 | 24:1 | 49:1 |
| 23 | 1:5 | BzMe$_3$NCl | 1 | 2.0 | 23:1 | 29:1 |
| 24 | 1:5 | (C$_7$H$_{15}$)$_4$NI | 1 | 0.5 | 40:1 | 44:1 |
| 25 | 1:10 | (C$_7$H$_{15}$)$_4$NI | 2 | 1.0 | 36:1 | 48:1 |
| 26 | 1:5 | (C$_{18}$H$_{37}$)$_2$Me$_2$NCl | 1 | 1.5 | 28:1 | 30:1 |
| 27 | 1:5 | (C$_{10}$H$_{21}$)$_3$MeNCl | 1 | 1.0 | 26:1 | 22:1 |
| 28 | 1:5 | (C$_{16}$H$_{33}$)Me$_3$NCl | 1 | 1.5 | 20:1 | 20:1 |

[1]Ratio of V:VI varied from 0.4:1 to 1.3:1.
[2]Reaction carried out at 120° C., initiators were benzyl triphenyl phosphonium chloride and n-butyl triphenyl phosphonium formate, respectively.
[3]Methyl bromoacetate used at 125° C.–130° C. in place of II.

EXAMPLE 29

An equimolar mixture of methyl phenyl carbonate and 2,4-dinitrochlorobenzene with 5 mole percent of added TBPB based on the carbonate was heated at 120° C. for 15 minutes. A 98 percent conversion of the carbonate with a 98 percent selectivity to 2,4-dinitrophenyl phenyl ether was obtained. Distillation of the product gave 5.6 g (86 percent yield) of the purified ether, b.p. 130° C.–135° C./0.2 mm.

EXAMPLE 30

A mixture of 3.8 g of methyl phenyl carbonate, 5.64 g of 4-chloro-3-nitrobenzotrifluoride, and 0.17 g of TBPB was heated at 150° C. for 1 hour. All of the carbonate was converted with a 99 percent yield of 2-nitro-4-trifluoromethylphenyl phenyl ether. Distillation of the product yielded 6.65 g (94 percent) of the ether, b.p. 148°–9° C./2 mm.

EXAMPLE 31

A reaction mixture of 3.8 g of methyl phenyl carbonate, 5.4 g of 2,3,5,6-tetrachloropyridine, and 0.17 g of TBPB was heated at 150° C. for 1 hour. The methyl phenyl carbonate was all converted with a 99 percent selectivity to 2-phenoxy-3,5,6-trichloropyridine. Distillation of the product gave 6.7 g (98 percent yield) of that ether, b.p. 135° C.–145° C./0.1 mm.

EXAMPLES 32–36

Mixtures of 0.01 g mole of a methyl phenyl carbonate, 0.01 g mole of 4-chloronitrobenzene, and 0.0002 g mole of a phosphonium salt initiator were heated at 155° C.–160° C. for 1 hour and product ratios in the following chemical equation were determined by nuclear magnetic resonance spectra integration.

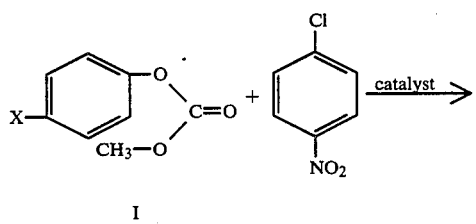

I

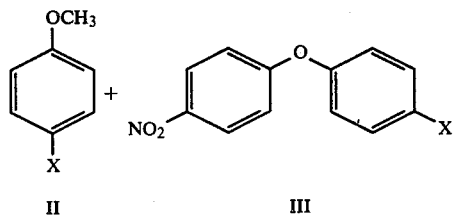

II     III

TABLE III

| Example No. | X | Phosphonium Initiator | % Conv. I | Mole Ratio II:III |
|---|---|---|---|---|
| 32 | OCH$_3$ | TBPB | 82 | 43:57 |
| 33 | H | TBPB | 100 | 40:60 |
| 34 | H | BuPh$_3$PHCO$_2$* | 96 | 29:71 |
| 35 | Cl | TBPB | 100 | 51:49 |
| 36 | NO$_2$ | TBPB | 100 | >98:2 |

*butyl triphenyl phosphonium formate

The nature of the substituent on the benzene ring of the methyl phenyl carbonate and the kind of quaternary salt initiator both had substantial effect on the proportion of the methyl phenyl carbonate reacting with the chloronitrobenzene to make the diaryl ether as compared to that undergoing the simple decomposition reaction to make an anisole.

In the same way as described and illustrated above, other monoethers and polyethers are prepared using the appropriate carbonate and halide reactants. For example, the bis(methyl carbonate) of bisphenol A is reacted with benzyl chloride to make the dibenzyl ether of bisphenol A. When the halide reactant is a reactive dihalide such as xylylene dichloride, the bisphenol A bis(methyl carbonate) reacts to form the polymeric xylylene-isopropylidenediphenylene polyether as shown in Example 37.

EXAMPLE 37

A mixture of 6.887 g (0.02 mole) of bisphenol A bis(methyl carbonate), 1.75 g each of α,α'-dichloro-o-xylene and α,α'-dichloro-p-xylene (0.02 mole total of xylene dichlorides), 0.14 g of TBPB and 25 ml of o-dichlorobenzene was heated at 150° C.–155° C. in a resin pot with vigorous mechanical stirring. After 4 hours, the liquid reaction mixture was removed from the resin pot and the solvent was evaporated at 100° C. under reduced pressure for 18 hours. The residue amounted to 6.8 g of a light yellow solid polymer which melted at 142° C.-–146° C. This polymer product had an inherent viscosity $\eta_{inh}$ at 25° C. in chloroform of 0.21 dl/g. The average molecular weight of the polymer was estimated by nuclear magnetic resonance spectroscopy to be about 7,000.

EXAMPLES 38–45

Alkali Metal Halide Initiators

A mixture of methyl phenyl carbonate (3.8 g, 0.025 mmole), benzyl chloride (3.16 g, 0.025 mole) and 1 mole of the alkali metal halide initiators further identified in Table IV were combined and heated at 160° C. for 2 hours. Results are contained in Table IV. Conversion indicates the percent of methyl phenyl carbonate reacted. Selectivity indicates the percent of phenyl benzyl ether formed compared to total products formed.

TABLE IV

| Example No. | Initiator | Solubilizing Agent | (mmole) | % Conversion | % Selectivity |
| --- | --- | --- | --- | --- | --- |
| 38 | LiCl | TP[1] | 1 | 17 | 96.7 |
| 39 | — | TP[1] | 1 | <1 | <1.0 |
| 40 | KI | 18-C-6[2] | 1 | 13 | 98.7 |
| 41 | LiCl | HMPA[3] | 1 | 38 | 95.7 |
| 42 | LiCl | HMPA[3] | 2 | 65 | 95.0 |
| 43 | LiCl | HMPA[3] | 3 | >98 | 92.4 |
| 44 | — | HMPA[3] | 2 | <1 | <1.0 |
| 45 | KI | HMPA[3] | 2 | 6 | 99.3 |

[1]triphenylphosphine oxide
[2]18-crown-6 (1,4,7,10,13,16-hexaoxacyclooctadecane)
[3]hexamethylphosphoramide

I claim:

1. A process for making an aryl ether of the empirical formula $Ar_nO_pR'_m$ which comprises contacting an aryl lower alkyl carbonate of the formula $Ar(OCO_2R)_m$ with an organic halide of the formula $R'X_n$ wherein Ar is a carbocyclic or heterocyclic aromatic group having a valence of m, R is a lower alkyl or halogenated lower alkyl group, R' is an aliphatic, cycloaliphatic, aromatic, or heterocyclic group having a valence of n, m and n each represent an integer from one to three, p is an integer equal to the product of m and n, and X is Cl, Br, or I, in the presence of a catalytic amount of an initiator at about 50° C.–250° C. and separating said aryl ether from the resulting reaction mixture.

2. The process of claim 1 wherein m and n are both one.

3. The process of claim 2 wherein R is a methyl group.

4. The process of claim 2 wherein X represents Cl.

5. The process of claim 2 wherein the temperature is about 100° C.–175° C.

6. The process of claim 2 wherein Ar is a polychlorophenyl group and R' is a methylenecarbonyloxyalkyl group.

7. The process of claim 2 wherein Ar is a polychloropyridyl group and R' is a methylenecarbonyloxyalkyl group.

8. The process of claim 1 wherein m is two and n is one.

9. The process of claim 1 wherein m and n are both two and the ether product is a polymeric polyether.

10. The process of claim 9 wherein Ar is an isopropylidenediphenylene group and R' is a xylylene group.

* * * * *